United States Patent [19]

Stokes et al.

[11] Patent Number: 5,433,734
[45] Date of Patent: Jul. 18, 1995

[54] TOOL-LESS THREADED CONNECTOR ASSEMBLY

[75] Inventors: Kenneth B. Stokes, Brooklyn Park; Richard H. Comben, St. Paul, both of Minn.

[73] Assignee: Medtronic, Inc., Minneapolis, Minn.

[21] Appl. No.: 180,164

[22] Filed: Jan. 11, 1994

Related U.S. Application Data

[62] Division of Ser. No. 879,656, May 6, 1992, Pat. No. 5,324,312.

[51] Int. Cl.⁶ ............................................. A61N 1/375
[52] U.S. Cl. ....................................................... 607/37
[58] Field of Search ...................... 128/642; 607/9, 36, 607/37, 115, 116, 119, 112

[56] References Cited

U.S. PATENT DOCUMENTS

| | | | |
|---|---|---|---|
| 3,437,091 | 12/1966 | Jerushalmi et al. | 607/122 |
| 4,411,277 | 10/1983 | Dickhudt | 607/116 |
| 4,538,623 | 9/1985 | Proctor et al. | 607/116 |

FOREIGN PATENT DOCUMENTS 0376904  4/1990  European Pat. Off. ........ A61N 1/36

*Primary Examiner*—Lee S. Cohen
*Assistant Examiner*—Jeffrey R. Jastrzab
*Attorney, Agent, or Firm*—Michael B. Atlass; Harold R. Patton

[57] ABSTRACT

A lead connection suitable for use in connecting a flexible coiled lead to an implantable device. The implantable device is provided with a threaded projection having an outer diameter sized with respect to the inner diameter of the lead's conductor coil to provide a secure interconnection therewith when attached thereto. The threaded projection is disposed on top and around a feedthrough pin projecting out of the implanted device's hermetic canister. The threaded projection is screwed into the conductor coil establishing sound electrical contact between the projection and the conductor. A strain relief collar surrounds the post and lead, and a twist-and-pull type connecting ring surrounds the base of the strain relief collar. The connecting post is prevented from being unscrewed from the conductor coil, since an unscrewing motion tends to tighten the conductor coil around the threaded post. Since no connecting structure is required at the connecting end of the lead, the lead can be cut to any appropriate length at the time of implant, thereby eliminating problems with excess implanted lead. If disconnection is required, the lead may be simply cut off just beyond the threaded connecting post, or the post may be unscrewed by applying inward radial or circumferential pressure on the conductor coils. In an alternative embodiment, the threaded projection is replaced with a tapered triangular post with either smooth or toothed edges, which is inserted into the coiled conductor lead.

2 Claims, 10 Drawing Sheets

TOOL-LESS THREADED CONNECTOR ASSEMBLY

This is a division of co-pending application Ser. No. 07/879,656, filed May 6, 1992 now U.S. Pat. No. 5,324,312.

FIELD OF THE INVENTION

This invention relates generally to the field of electrical connectors, and more particularly relates to a method and apparatus for establishing a mechanical and an electrical connection between a conductive lead and an electronic apparatus.

BACKGROUND OF THE INVENTION

A multitude of devices are known for which an electrical and mechanical coupling between a conductive lead and an electronic component must be established. For example, implantable medical devices such as cardiac pacemakers, cardioverters, defibrillators, neural stimulators, and the like, must be electrically and mechanically connected to one end of an electrical lead. In the case of an implantable medical device, there are particularly stringent design criteria with regard to the mechanical and electrical properties of the lead connection (i.e., the connection between a conductive lead and the device itself). In particular, the lead connection for an implantable device should preferably be highly reliable, both from a mechanical and from an electrical point of view. Any physical structure used in an implantable device lead connection should be small, lightweight, and biologically inert. A lead connection should preferably be capable of withstanding repeated flexing of the lead with respect to the device itself; this consideration is one reason that implantable leads are frequently of a coiled conductor type. Also, the lead connection should be strong enough to resist disconnection due to the various forces that may be exerted on the lead connection when implanted in a human body. Furthermore, since the implantation of a medical device is a delicate surgical process, the lead connection should be relatively simple to effectuate in the surgical environment.

Implanted medical devices such as pacemakers are battery-powered electronic devices which are susceptible to breakage, failure, or battery depletion. Thus, these devices may occasionally need to be explanted and/or replaced. Often, though, a lead associated with a device need not be removed along with the device. The previously implanted lead may be functioning adequately and may have even become ingrown within human tissue, making lead removal undesirable. Consequently, a further preferable feature of a lead connection for an implantable pulse generator is that it should allow for disconnection without damage to either the lead or the generator, in order that it may be removed and/or replaced without removal or replacement of the lead.

One prevalent means in the prior art for establishing the electrical and mechanical connection between a lead and an implantable pulse generator has been to provide a connector with molded-in connector blocks containing set screws. A terminal pin provided at the terminal end of the lead is received in a terminal receptacle in the connector, and the lead is then secured in place by tightening the set screws, which may also provide the requisite electrical contact between the lead conductor and the pacemaker's hermetic feedthrough elements.

With conventional connector and set screw lead connecting arrangements, proper tightening of the set screws is of critical importance. Over-torquing of a set screw can cause stripping of the set-screw threads or damage to the lead terminal or lead conductor. On the other hand, under-torquing of the set screw can lead to post-implant problems, since the lead terminal may become disengaged from the connector receptacle. In some cases, therefore, a specially designed set-screw driver or other tool may be provided as a means to ensure proper tightening. For instance, the tool may be designed to "break away" or flex after a proper amount of torque has been applied to the set screw.

A further complication with set-screw-type lead connector arrangements is that after tightening, the set screw must be sealed from bodily fluids which could cause corrosion or short-circuiting of the connector top or feed through. This sealing is typically accomplished through the use of grommets, which may be damaged during tightening of the set screw.

Several other techniques in the prior art for establishing the electrical and mechanical connection of a lead and an implantable medical device are briefly described in U.S. Pat. No. 4,540,236 to Peers-Trevarton, which patent is hereby incorporated by reference.

Implantable medical devices are typically implanted subcutaneously and may be implanted in a patient for many years. Accordingly, both for cosmetic reasons and for avoiding discomfort and pocket erosion at the implant site, it has always been an objective in the design of implantable devices that the devices be as small and lightweight as possible. In recent years, improvements in various technological fields, particularly those in the field of electronics, have enabled fully-featured implantable devices to be made smaller and smaller. It is believed by the inventors, for example, that a single-chamber demand pacemaker weighing less than five grams, approximately 2.8 centimeters in diameter, and having a volume of approximately 2.5 cubic centimeters is technologically feasible and could soon be commercially available. A conventional connector, even in its smallest practical configuration, would be larger and possibly heavier than an implantable device of such dimensions. The practical limitations on the miniaturization of a connector arise from the fact that the connector's set screws must not be made so small as to become difficult to seat a tool and tighten, or to become insufficiently strong. There are similar limitations on the miniaturization of other types of lead connection structures.

For any type of lead connection which requires a lead terminal to be disposed at the connected end of the lead, the length of the lead is determined at the time of manufacture of the lead, and cannot be changed at the time of implant. Since every patient's anatomy is unique and the implant site of a pacemaker may vary from patient to patient, there is typically some excess length of lead when a fixed-length lead is implanted. Typically, the excess length of lead is gathered together or simply wrapped around the implanted device. This can result in problems such as discomfort to the patient, lead failure due to kinks or bends in the excess length of lead, or displacement of the lead due to forces exerted on the excess length of lead. Additionally, the excess lead wrap may adversely effect the function of activity-based pulse generators by lying across the sensor-carrying face of the generator's housing.

It is believed by the inventors, therefore, that there exists a need for an alternative lead connection arrangement which is readily adaptable to smaller implantable devices. It is also believed by the inventors that it would be advantageous to provide a lead connection arrangement in which the length of the implanted lead can be customized for each patient.

SUMMARY OF THE INVENTION

An alternative to the conventional means for establishing a mechanical and electrical coupling between a coiled conductive lead and an electronic device is provided by the threaded connector assembly of the present invention, in which a pin projecting out of the electronic device is threaded so as to engage the conductor coils of the lead. The threaded pin, being slightly oversized with respect to the inner diameter of the conductor coils, expands the coils slightly as it is screwed in, assuring faultless electrical contact between the conductor and the screw.

Unlike a conventional bolt and nut arrangement, a screw and coil do not come apart by torquing. Application of a withdrawal torquing force (i.e., torque in the opposite rotational direction from that used to insert the screw into the coil) causes the coil to reduce in diameter, thereby increasing the clamping force of the coil around the threaded pin.

If it becomes necessary to disengage the pin from the lead coil, for example to reposition the lead or replace the implantable device, one may grip the coil firmly to prevent the compression of the coil around the pin as the pin is torqued out. Alternatively, one may simply cut the lead off near the projecting end of the pin and then remove the remaining portion of the coil either by pulling with enough force to straighten the conductor forming the coil, or by unwinding the lead conductor from around the threaded pin. While the former method has the advantage of not destroying any amount of the conductor coil, the amount of conductor coil destroyed in the latter method is minimal, since only the coiled length of the conductor which is in contact with the projecting pin is lost (assuming that the lead is cut at the very end of the pin).

Since the lead connection in accordance with the present invention does not require the provision of a terminal at the connected end of the lead, the lead may be cut to an appropriate length to minimize excess lengths of lead in each patient. An excessively long lead may be initially introduced into the patient, with the excess length being helpful to the physician in facilitating proper placement of the lead. After the lead has been positioned, any excess length of lead may be simply cut away.

In an alternative embodiment of the present invention, a tapered triangular connecting post is substituted in place of the threaded connector pin. A coiled conductor lead is coupled to the tapered triangular connecting post by forcing the tapered pin axially into the coiled conductor, with or without rotational or screwing force. The tapered triangular pin may be provided with teeth along its edges for ensuring a secure connection between the pin and the coiled conductor.

In either of the above-noted embodiments, a lead connection in accordance with the present invention is seared and sealed by means of a bayonet-type collar surrounding a flexible strain relief collar, through which the coiled conductor lead is threaded.

BRIEF DESCRIPTION OF THE DRAWINGS

The foregoing and other features of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
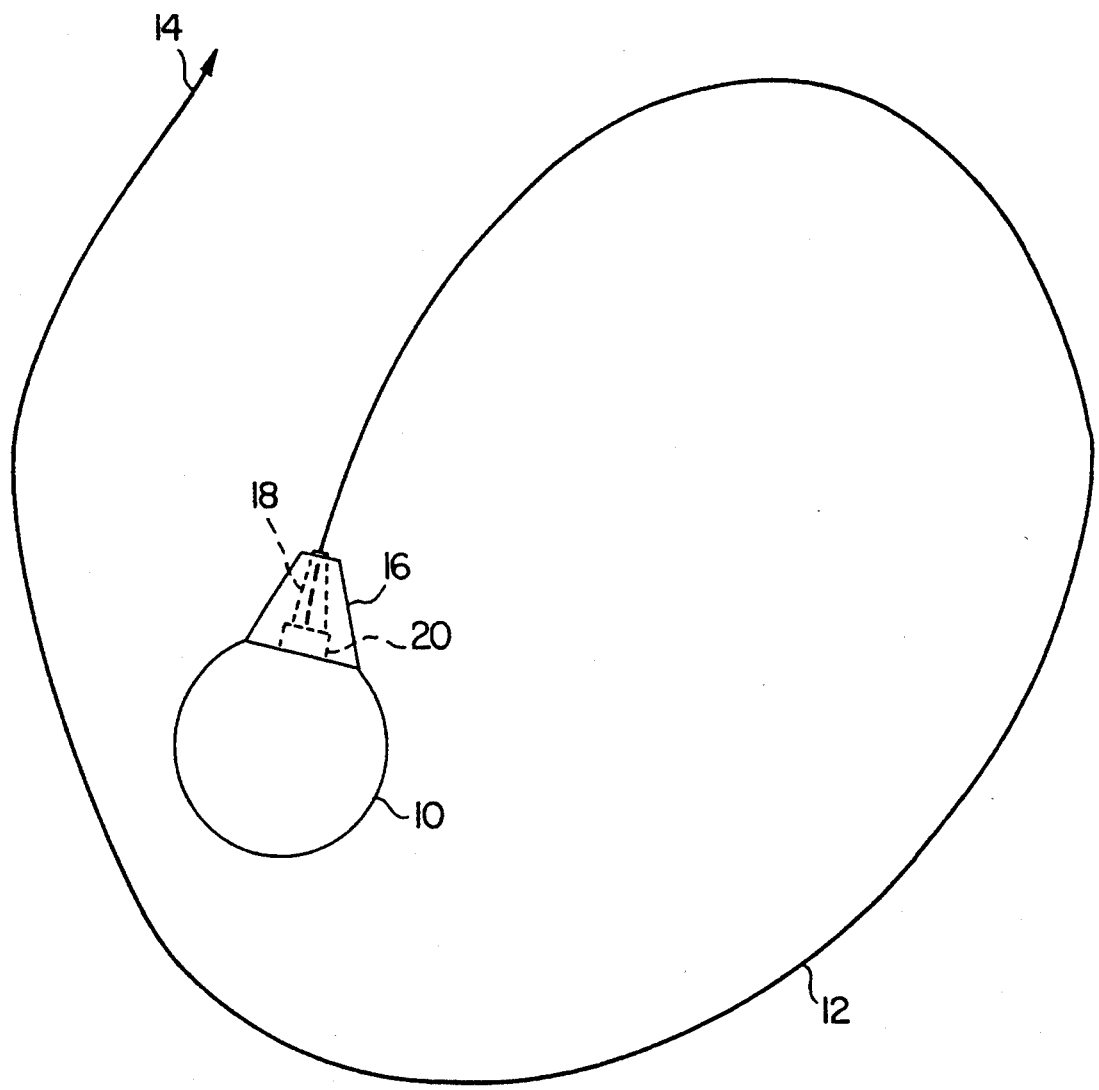
FIG. 1 is a diagram of a pacemaker and lead connected in accordance with one embodiment of the present invention.

In FIG. 1, a pacemaker 10 and pacemaker lead 12 connected in accordance with one embodiment of the present invention are shown. In the presently disclosed embodiment of the invention, pacemaker 10 is a highly miniaturized, fully programmable, single-chamber (i.e., VVI or AAI) device weighing approximately five grams or so. The hermetically sealed outer canister of pacemaker 10 has a diameter of approximately 2.8 centimeters and has a volume of about 2.5 cubic centimeters.

Lead 12 in FIG. 1 is a conventional unipolar pacing/sensing lead of the coiled conductor type. Such a lead is well-known in the field, and is disclosed, for example, in U.S. Pat. No. 3,939,843 issued to Smyth, which patent is hereby incorporated by reference in its entirety. Typically, lead 12 is implanted with conventional catheterization techniques so that the distal end 14 of lead 12 is introduced into the atrium or ventricle of a patient's heart. Distal end 14 of lead 12 has an exposed electrode thereon for applying cardiac pacing pulses, or sensing cardiac signals, as is well-known in the field.

Although the present invention is being described in the context of a single chamber pacemaker, it is to be understood that the lead connection arrangement of the present invention is equally applicable in dual-chamber pacemakers and in other situations calling for connection of a lead to a device, including but not limited to cardioverters, defibrillators, neural stimulators, and the like.

With continued reference to FIG. 1, a bayonet-type fastening collar 16 is engaged on pins diametrically disposed on a disk-shaped connector platform, as shall be hereinafter shown and described in greater detail with reference to FIGS. 3 through 5. Bayonet collar 16 is preferably made of a suitable bio-compatible material such as titanium, epoxy, polyurethane, polysulfone, or the like, in accordance with common practice in the art. Bayonet collar 16 surrounds a strain relief collar 18 (shown in phantom in FIG. 1 since it is hidden from view by bayonet collar 16), which may be made of silicone rubber or another suitably resilient and biologically inert material, as would be apparent to one of skill in the art. Strain relief collar 18 has a cylindrical bore and integrally formed sealing rings along its axis, as will be hereinafter described with reference to FIGS. 7 and 8.

Figure 2:
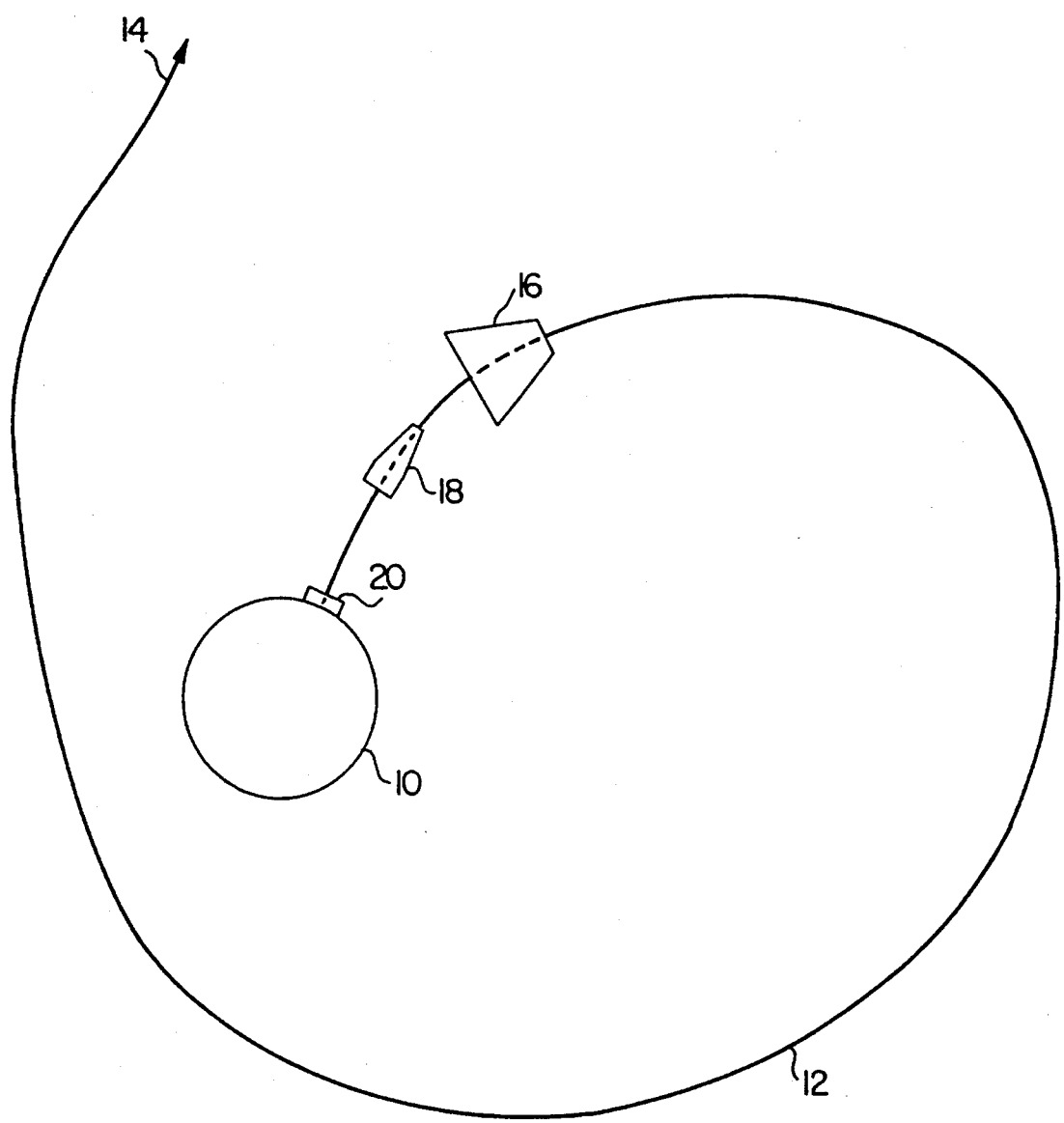
FIG. 2 is a diagram of the pacemaker and lead of FIG. 1 in a partially disconnected state.

Turning to FIG. 2, the pacemaker assembly of FIG. 1 is shown in a partially disconnected state. In FIG. 2, bayonet collar 16 has been disengaged from connector platform 20. Also in FIG. 2, strain relief collar 18 has been slid away from connector platform 20.

Figure 3:
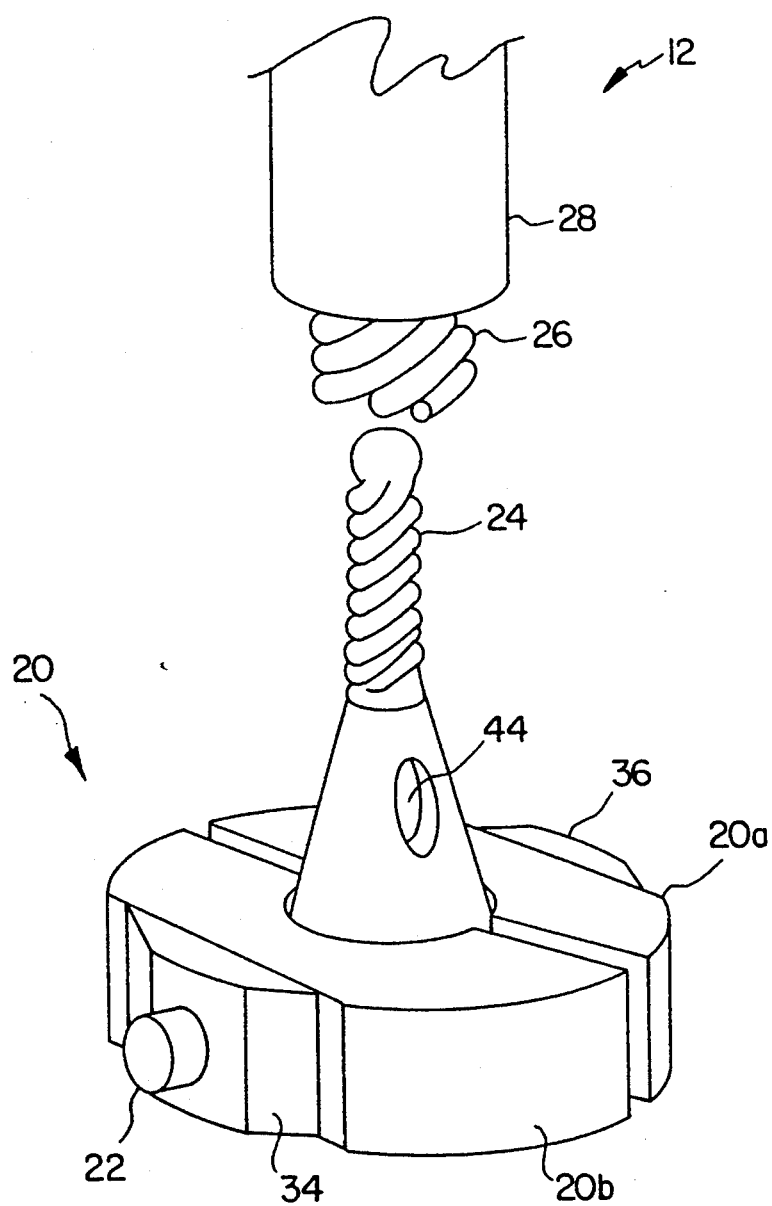
FIG. 3 is an enlarged perspective view of a connecting post and connecting platform disposed on the pacemaker of FIG. 1 and 2.
Figure 4:
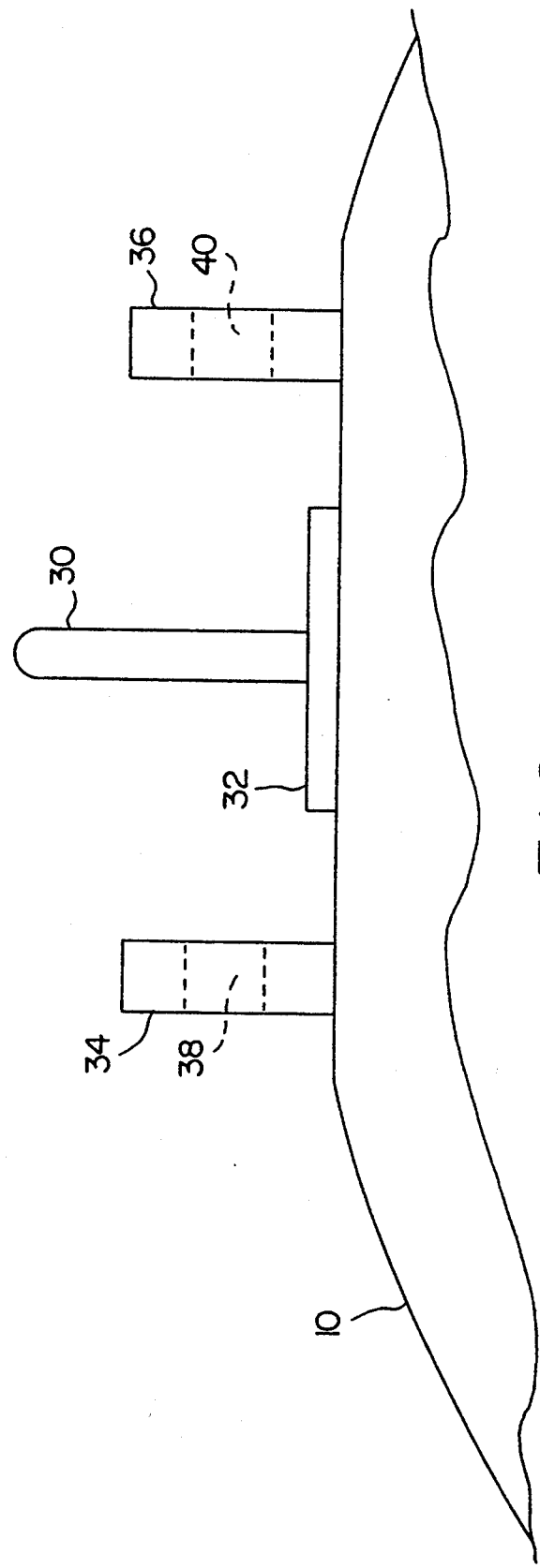
FIG. 4 is an enlarged cross-sectional view of the lead connection of FIGS. 1 through 3 in an intermediate stage of assembly and connection.

In FIG. 3, a greatly enlarged perspective view of connector platform 20 and a portion of lead 12 is shown. As can be seen in FIG. 3, connector platform 20 actually comprises two substantially semi-circular platform halves 20a and 20b, disposed between opposing supporting members 34 and 36. Supporting members 34 and 36 each have an outwardly projecting bayonet pin 22 (only one of which is visible in the perspective view of FIG. 3), which are engaged in L-shaped grooves in bayonet collar 16, as will be apparent in later Figures. Projecting perpendicularly upward from inbetween connector platform halves 20a and 20b is a threaded connector post 24. As will hereinafter become apparent with reference to FIGS. 4, 5, 6, 7, and 9, connector post 24 is held in contact with a feedthrough terminal projecting out of pacemaker 10.

The process of connecting lead 12 to pacemaker 10 in accordance with the presently disclosed embodiment of the invention begins with inserting the proximal end of lead 12 (i.e., the end to be connected to pacemaker 10) first through bayonet collar 16 and then through strain relief collar 18. Bayonet collar 16 and strain relief collar 18 are not shown in FIG. 3, but are assumed to be disposed along the length of lead 12 as shown in FIG. 2.

As shown in FIG. 3, lead 12 is of the coiled conductor type, as is typical of implantable leads. Lead 12 thus comprises a coiled conductor 26 surrounded by a resilient protective shielding 28, which may be silicone rubber or the like, as is commonly used in the art. The connection in accordance with the present invention involves screwing threaded connector post 24 axially into coiled conductor 26. This may be accomplished by either turning lead 12 with respect to post 24, or turning pacemaker 10 with respect to lead 12. Since lead 12 will typically be implanted prior to connection with pacemaker 10, the latter method (in which the pacemaker is turned with respect to the lead) is preferable.

Once pin 24 has been screwed into the coiled conductor of lead 12, strain relief collar 18 is slid into place directly above platform 20 and surrounding pin 24 and the terminal end of lead 12. Finally bayonet collar 16 is slid down around strain relief collar and engaged on bayonet pins 22.

The manner in which threaded pin 24, connector platform halves 20a and 20b. and connector pins 22 are assembled during manufacture according to the presently disclosed embodiment of the invention will now be described with reference to the cross-sectional view of FIG. 4. FIG. 4 shows a feedthrough terminal 30 projecting upward out of the top of pacemaker 10. As would be known to one of ordinary skill in the implantable device field, a feedthrough is required to allow electrical contact between the hermetically sealed internal circuitry and a pacing/sensing lead. In accordance with common practice in the art, feedthrough terminal pin 30 is in electrical contact with internal pacemaker circuitry (not shown in the Figures) but is electrically isolated from the outer canister of pacemaker 10. An insulating and/or supporting portion 32 of the feedthrough mechanism is visible in FIG. 4. It is believed by the inventors that any of several known feedthrough arrangements would be suitable for the purposes of practicing the present invention. It is further believed that the use of a particular feedthrough arrangement is not critical to the present invention, and that selection of one of several known feedthrough arrangements would be a matter of routine to a person of ordinary skill in the art.

Figure 5:
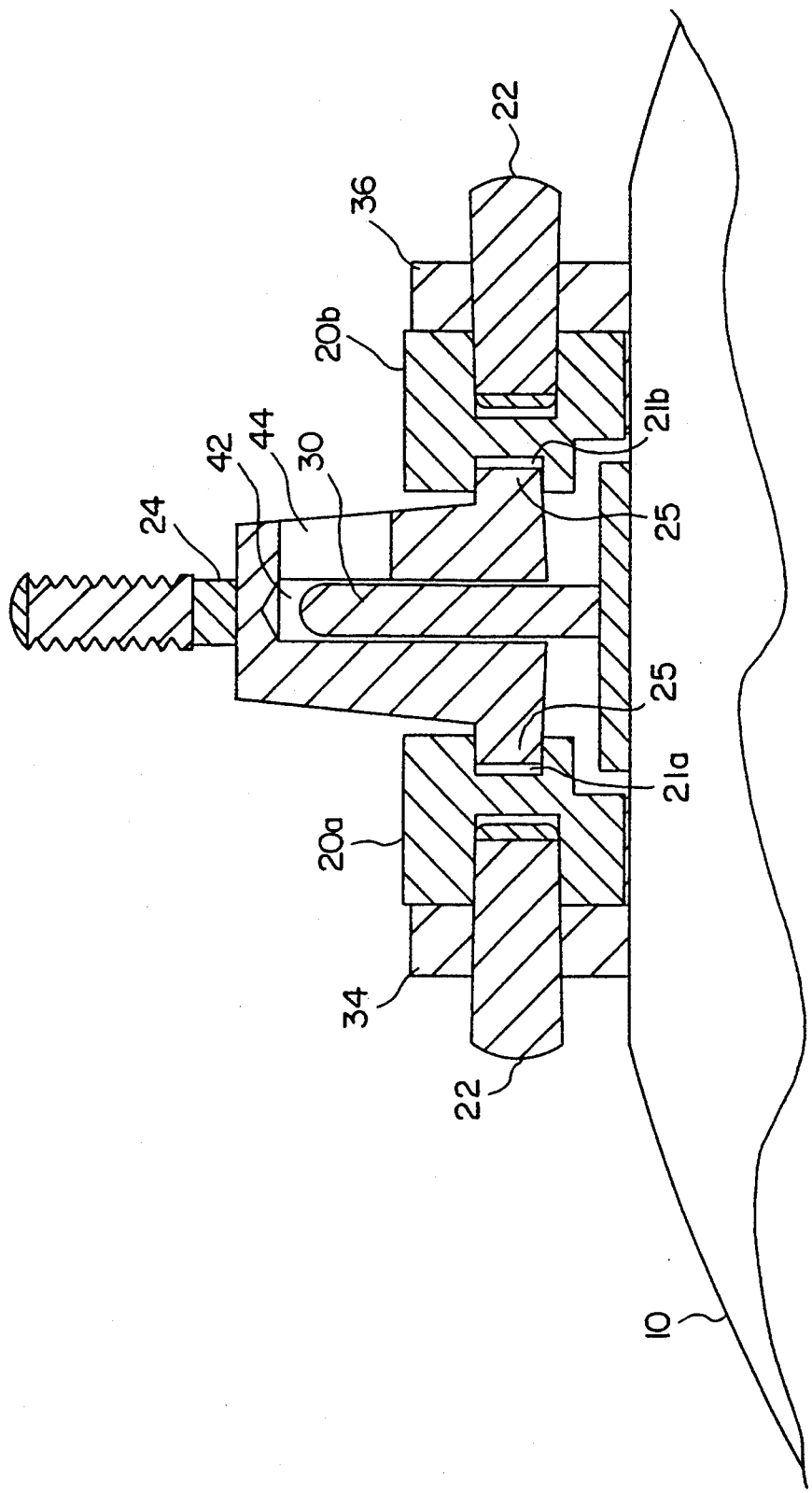
FIG. 5 is an enlarged cross-sectional view of the lead connection of FIGS. 1 through 4 in another intermediate stage of assembly and connection.

Supporting members 34 and 36 are also visible in the cross-sectional view of FIG. 5. A cylindrical bore 38 through support 34, and a similar bore 40 through support 36 are provided to receive the bayonet mounting pins 22, as shown in FIG. 3. For clarity, semicircular platform halves 20a and 20b are cross-hatched in FIG. 5. A cylindrical bore in each connector half 20a and 20b is aligned with cylindrical bores 38 and 40 in supporting members 34 and 36, so that tapered mounting pins 22 may be inserted therethrough. Threaded connector post 24 has a tapered flange 25 around its base which is received in conforming cavities 21a and 21b in respective connector halves 20a and 20b. In addition, connector post 24 has a cylindrical bore 42 which allows feedthrough terminal pin 30 to be snugly received in, allowing for permanent connection (e.g., welding, staking) via cylindrical cavity 44 and making electrical contact with connector post 24.

FIG. 5 depicts the connector assembly of pacemaker 10 as it would appear at the end of the manufacturing stage, with the fit of platform halves 20a and 20b, connector post 24, and pins 22 being such that these components, once assembled as shown in FIG. 5, are rigidly secured in place.

Figure 6:
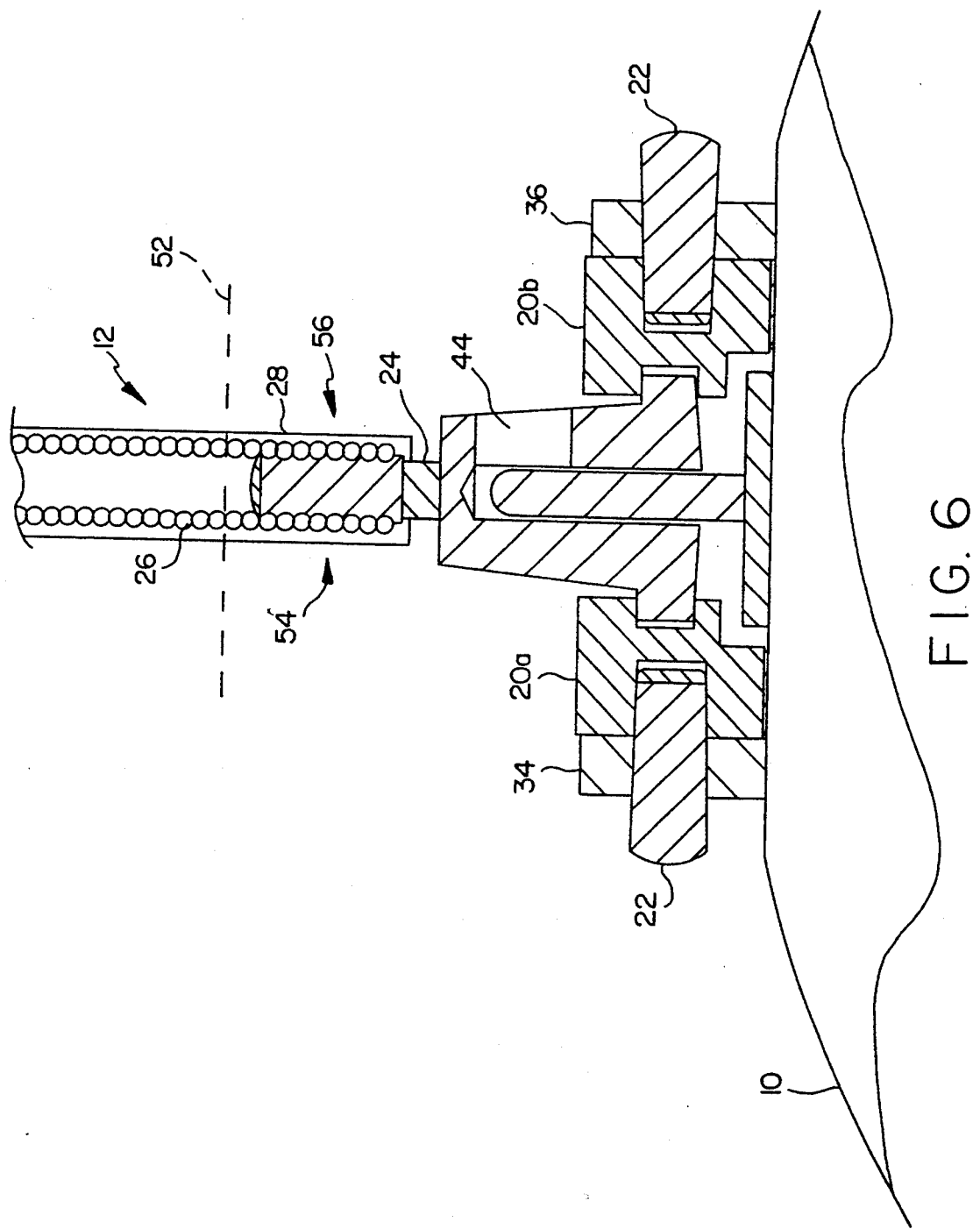
FIG. 6 is an enlarged cross-sectional view of the lead connection of FIGS. 1 through 5 in another intermediate stage of assembly and connection.

In FIG. 6, lead 12 is shown having been screwed onto threaded post 24 as previously described.

Figure 7:
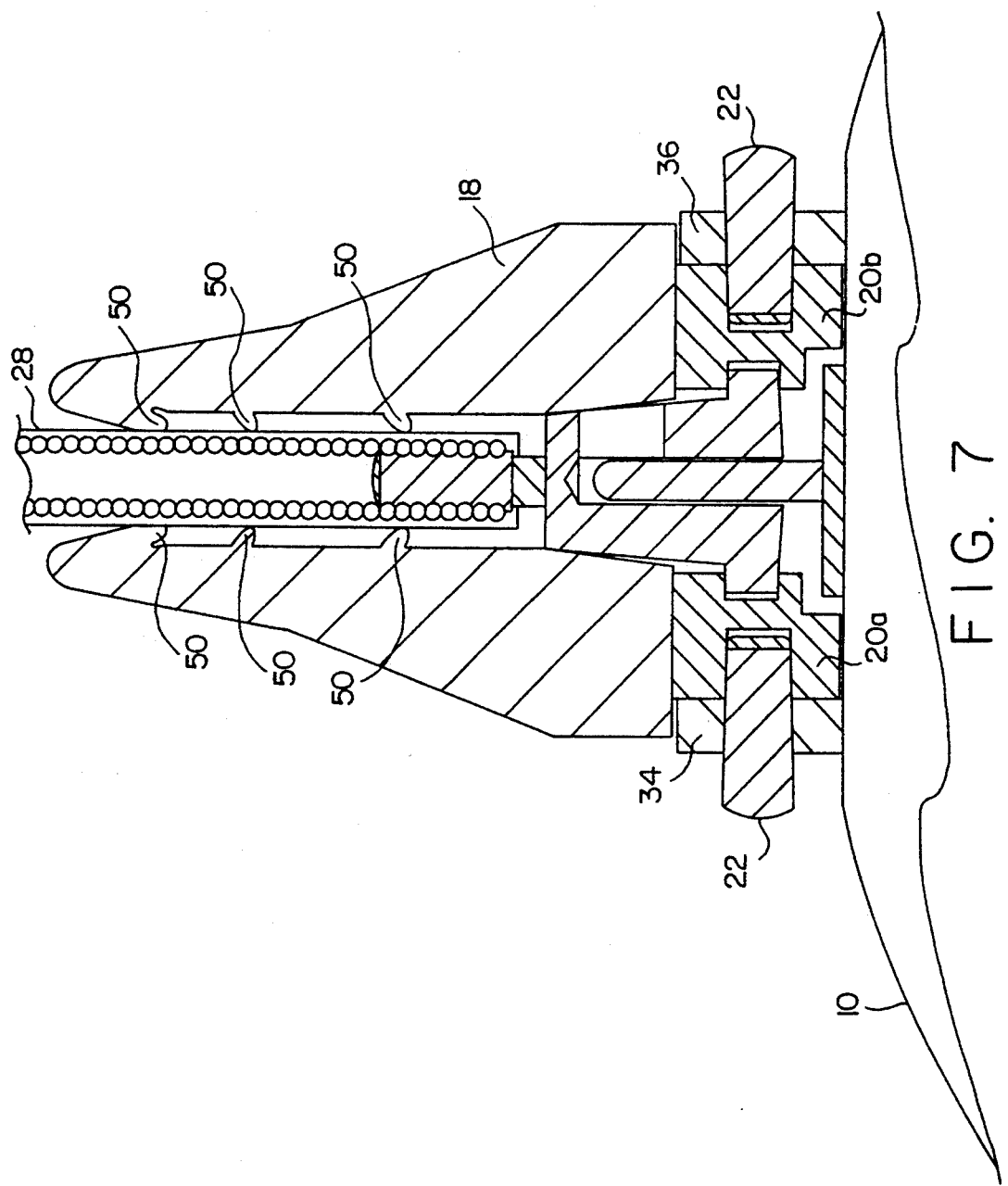
FIG. 7 is an enlarged cross-sectional view of the lead connection of FIGS. 1 through 6 in another intermediate stage of assembly and connection.
Figure 8:
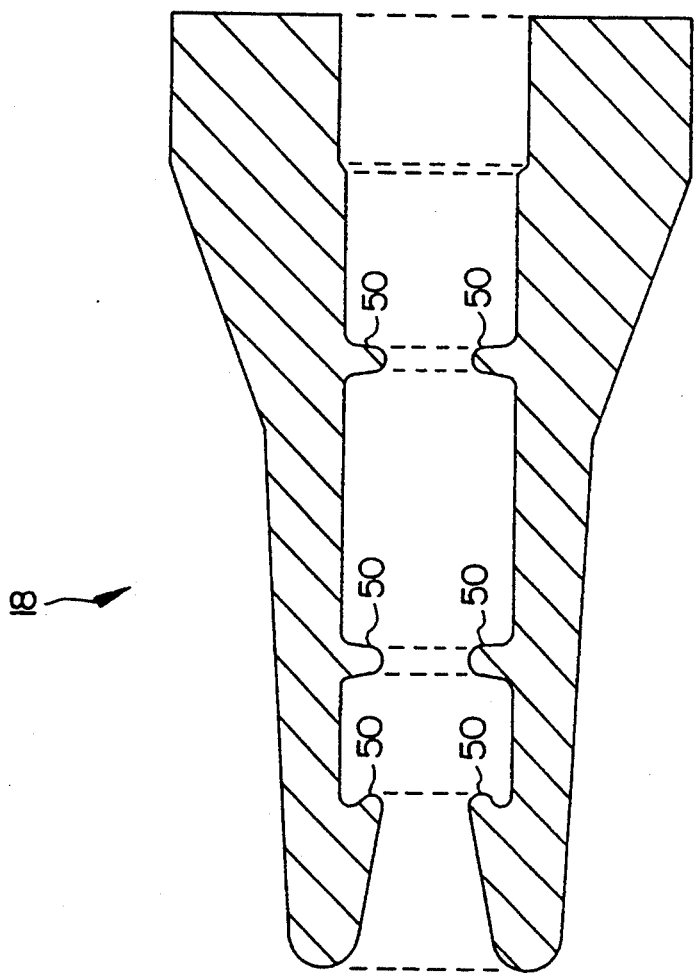
FIG. 8 is an enlarged cross-sectional view of the strain relief collar of FIGS. 1 and 2.

In FIG. 7, strain relief collar 18 has been slid along lead 12 and into place around lead 12 and post 24. Of course, it is to be understood that strain relief collar 18 would have been threaded onto the terminal end of lead 12, along with bayonet collar 16, prior to screwing lead 12 onto threaded post 24. A greatly enlarged cross-sectional view of strain relief collar 18 is shown in FIG. 8. As shown in FIG. 8, strain relief collar 18 is provided with several integrally formed sealing rings along its central cylindrical bore. Sealing rings 50 form a fluid-tight seal against protective shielding 28 of lead 12 when lead 12 is inserted through collar 18. The sealing of collar 18 against shielding 28 of lead 12 can perhaps best be appreciated with reference to FIG. 7.

Figure 9:
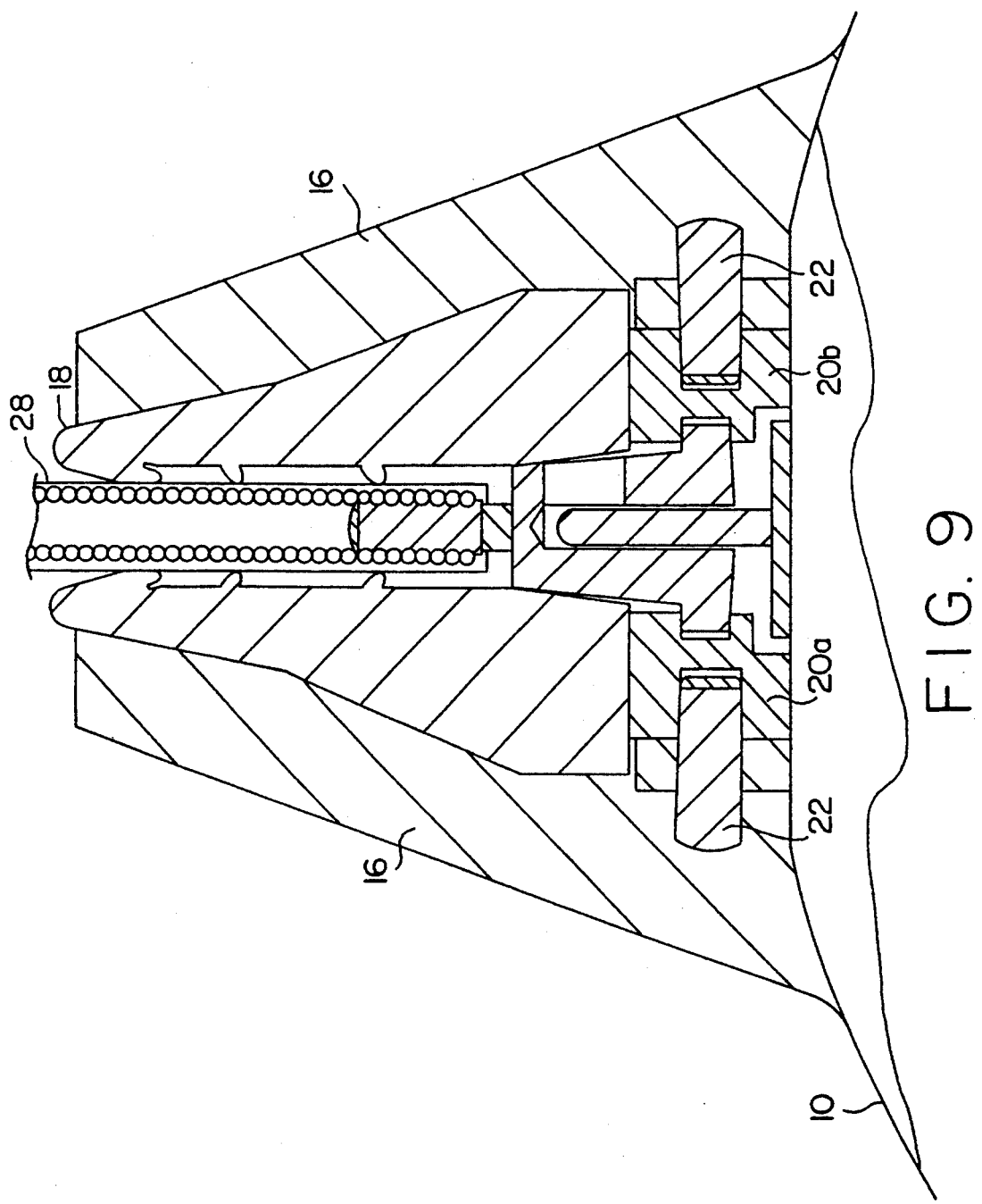
FIG. 9 is an enlarged cross-sectional view of the lead connection of FIGS. 1–7 in its final stage of assembly and connection.

In FIG. 9, bayonet collar 16 is shown having been engaged, in a conventional bayonet arrangement, around bayonet pins 22. This constitutes the final step in implementing the lead connection in accordance with the disclosed embodiment of the invention.

As previously noted, one advantage of the lead connection arrangement presently disclosed is that no terminal or other connection structure is required to be disposed at the connecting end of lead 12. Since any point along the length of lead 12 is suitable for connection in the manner just described with reference to FIGS. 1 through 9, lead 12 may be cut to a suitable length (as with scissors) at any point. This eliminates the problem of excess lengths of lead in a patient. After lead 12 is implanted in a patient using conventional catheterization techniques, the connecting end 12 may be chosen to be at any point along the length of lead 12. When the lead has been cut to a desired length, the implanted device (in the above, embodiment, pacemaker 10) is then screwed into the lead, as described above.

Should it become necessary to disconnect pacemaker 10 from lead 12 after connection in the manner shown in FIG. 9, there are two possibilities. In the first method, collar 16 may be disengaged from pins 22 and pulled away from the connecting area, and collar 18 similarly slid along lead 12 away from the connecting area, resulting in the situation depicted in FIG. 6. Then, lead 12 may be simply cut off, at the point designated in FIG. 6 by dashed line 52. This leaves a small remainder of coiled conductor 26 wound around post 24; this remainder of lead 12 may be pulled away from post 24 (with enough force to straighten conductor 26), or unwound from post 24, and discarded. In the second disconnection method, bayonet collar 16 and strain relief collar 18 are first slid off as before to yield the situation depicted in FIG. 6. Then, opposing pressure from the thumb and forefinger is exerted on the portion of coiled conductor 26 surrounding post 24, in the regions designated generally by arrows 54 and 56 in FIG. 6. As this pressure is applied, post 24 may be unscrewed from coiled conductor 26. The tightening or clamping effect that would otherwise prevent post 24 from being unscrewed is avoided by the pressure exerted at points 54 and 56, as this pressure prevents the constricting of the coils of conductor 26. If pressure is not exerted as shown in FIG. 6, attempting to unscrew post 24 from coiled conductor 26 would cause the coils of conductor 26 to constrict around post 24, as previously noted.

From the foregoing detailed description of a preferred embodiment of the invention, it should be apparent that a lead connection arrangement particularly suitable for use with implanted medical devices has been disclosed. Although a particular embodiment of the invention has been described in detail, this has been for the purposes of illustration only. It is to be understood that various alterations, substitutions, or modifications may be made to the disclosed embodiment without departing from the spirit and scope of the appended claims, which follow.

Figure 10:
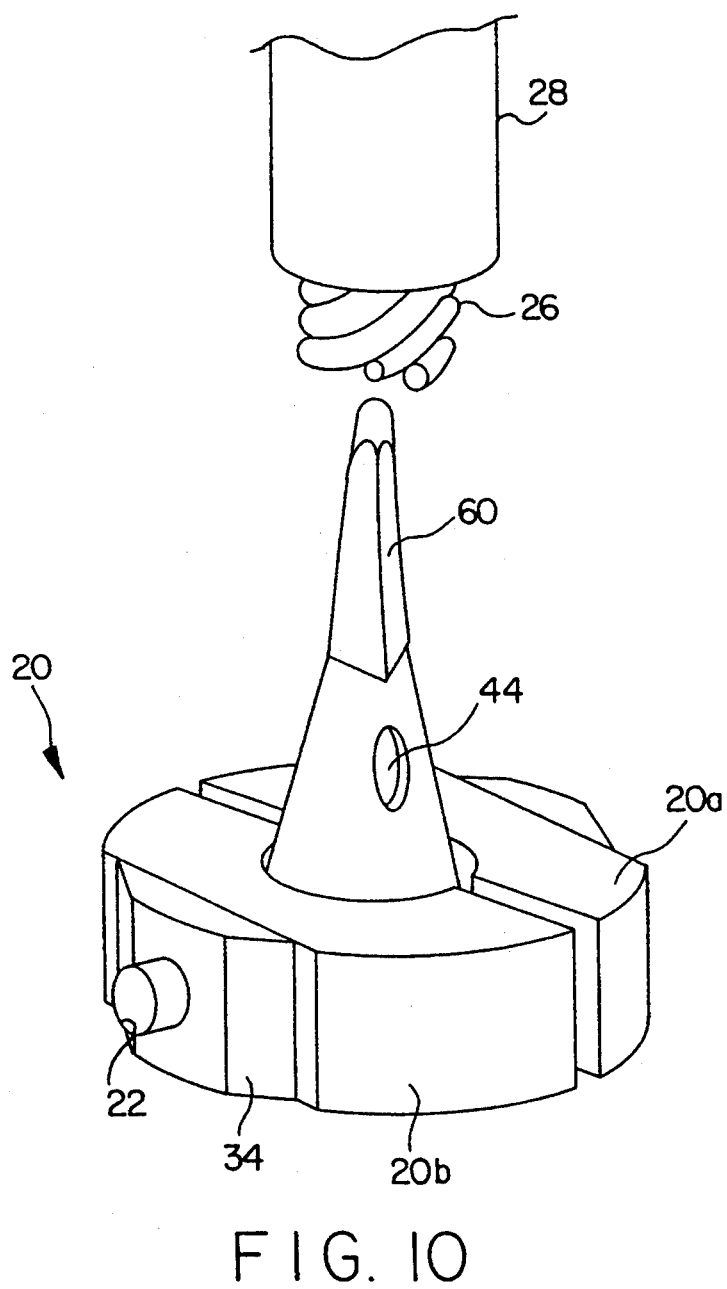
FIG. 10 is an enlarged perspective view of an alternative embodiment of the threaded connecting post of FIGS. 1 and 2.

In particular, with regard to alternatives available in the practice of the invention, the inventors have contemplated a modification to the above-described embodiment in which terminal post 24 is replaced with a tapered triangle pin 60 such as is depicted in FIG. 10. In FIG. 10, it is to be understood that components therein which are identical to components in the previously disclosed embodiment have retained the same reference numerals as in FIGS. 1–9.

Figure 11:
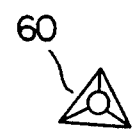
FIG. 11 is a perspective view from above of the triangular connecting post of FIG. 10.
Figure 12:
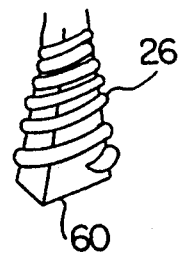
FIG. 12 is a perspective view of the coiled lead conductor from FIGS. 1 and 2 wrapped around the triangular connecting post of FIGS. 10 and 11.
Figure 13:
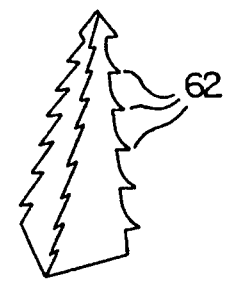
FIG. 13 is a perspective view of an alternative embodiment of the triangular connecting pin of FIGS. 10 through 12.

In FIG. 10, threaded terminal post 24 has been replaced with tapered triangle connector pin 60. A view of pin 60 from above looking straight downward is shown in FIG. 11. For the embodiment of FIG. 10, lead 12 is attached to tapered triangle terminal pin 60 by pushing coiled conductor 26 straight down around pin 60, that is, without rotation of lead 12. Alternatively, the generator may be screwed into the lead. However, the push on feature is required for bipolar or multipolar lead connection. The tapered shape of pin 60 causes coiled conductor 26 to be secured to pin 60 by compressing around it, as shown in FIG. 12. If desired, tapered pin 60 may further be provided with teeth 62 along its edges, as depicted in FIG. 13. Teeth 62 would serve a similar function to the threads of connector pin 24, namely to grip the windings of coiled conductor 26. As with threaded connector pin 24, lead 12 may be removed from triangular pin 60 by either pulling and unwinding, or by unscrewing.

What is claimed is:

1. A pacemaker, comprising a pulse generator in a hermetic container having a connector means for connection to a pacemaker lead, said connector means comprising a tapered triangular connector post sized to be received within a bore of a coiled conductor within a pacemaker lead upon said connector post being forced axially into said bore and to grip the lead by inducing a tightening of said coiled conductor around said connector post.

2. A pacemaker in accordance with claim 1 wherein said tapered triangular connector post has teeth along edges thereof for engaging coils of said coiled conductor upon said connector post being forced axially into said bore.

* * * * *